(12) United States Patent
Magno et al.

(10) Patent No.: US 11,076,982 B2
(45) Date of Patent: Aug. 3, 2021

(54) FALLOPIAN BIOCOMPATIBLE PLUG WITH DIFFERENTLY EXPANDABLE PORTIONS

(71) Applicant: Gyrus ACMI, Inc., Southborough, MA (US)

(72) Inventors: Joey Magno, Cordova, TN (US); Eric A. Gilbert, Cordova, TN (US); Rachel M. McGuire, Cordova, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 466 days.

(21) Appl. No.: 15/857,915

(22) Filed: Dec. 29, 2017

(65) Prior Publication Data

US 2019/0201233 A1  Jul. 4, 2019

(51) Int. Cl.

| A61F 6/22 | (2006.01) |
|---|---|
| A61B 17/12 | (2006.01) |
| A61B 1/313 | (2006.01) |
| A61B 17/00 | (2006.01) |
| A61L 31/14 | (2006.01) |
| A61L 31/04 | (2006.01) |
| A61B 1/018 | (2006.01) |

(Continued)

(52) U.S. Cl.
CPC ............... *A61F 6/22* (2013.01); *A61B 1/018* (2013.01); *A61B 1/3132* (2013.01); *A61B 17/1219* (2013.01); *A61B 17/12159* (2013.01); *A61B 17/12163* (2013.01); *A61L 31/042* (2013.01); *A61L 31/044* (2013.01); *A61L 31/045* (2013.01); *A61L 31/047* (2013.01); *A61L 31/146* (2013.01); *A61L 31/148* (2013.01); *A61B 1/303* (2013.01); *A61B 2017/00004* (2013.01); *A61B 2017/0034* (2013.01); *A61B 2017/1205* (2013.01); *A61B 2017/4216* (2013.01)

(58) Field of Classification Search
CPC combination set(s) only.
See application file for complete search history.

(56) References Cited

U.S. PATENT DOCUMENTS 5,954,715 A * 9/1999 Harrington ...... A61B 17/12109
128/831
6,145,505 A * 11/2000 Nikolchev ....... A61B 17/12099
128/830

(Continued)

FOREIGN PATENT DOCUMENTS

WO  90/02525  3/1990
WO  2010/036721 A2  4/2010

*Primary Examiner* — John P Leubecker
*Assistant Examiner* — Shankar Raj Ghimire
(74) *Attorney, Agent, or Firm* — Schwegman Lundberg & Woessner, P.A.

(57) ABSTRACT

A fallopian biocompatible plug can include differently expandable portions. A method of treating a uterine abnormality of a patient includes: providing an endoscope having a working channel; inflating a uterine cavity with a fluid; delivering a biocompatible plug into an ostium of a fallopian tube of the patient, wherein the biocompatible plug is substantially cylindrical in form and configured to be radially expandable, wherein the biocompatible plug is configured to expand in the ostium of the fallopian tube to seal the fallopian tube from the uterine cavity; delivering a resection device through the working channel; and resecting the uterine abnormality.

20 Claims, 9 Drawing Sheets

(51) Int. Cl.
  *A61B 17/42*  (2006.01)
  *A61B 1/303*  (2006.01)

(56) References Cited

U.S. PATENT DOCUMENTS

| | | | | |
|---|---|---|---|---|
| 6,526,979 | B1* | 3/2003 | Nikolchev | A61B 17/12022 |
| | | | | 128/830 |
| 7,842,035 | B2* | 11/2010 | Harrington | A61B 17/12022 |
| | | | | 606/32 |
| 8,235,047 | B2* | 8/2012 | Swann | A61B 17/1219 |
| | | | | 128/831 |
| 8,322,341 | B2* | 12/2012 | Koeller | A61F 6/22 |
| | | | | 128/830 |
| 8,347,887 | B2* | 1/2013 | Chapman | A61B 17/11 |
| | | | | 128/830 |
| 8,356,600 | B2* | 1/2013 | Frigstad | A61F 6/22 |
| | | | | 128/831 |
| 9,392,935 | B2 | 7/2016 | Adams et al. | |
| 2002/0013589 | A1* | 1/2002 | Callister | A61B 17/12022 |
| | | | | 606/108 |
| 2002/0029051 | A1* | 3/2002 | Callister | A61F 6/225 |
| | | | | 606/157 |
| 2007/0191768 | A1* | 8/2007 | Kolb | A61B 17/12159 |
| | | | | 604/104 |
| 2009/0048685 | A1* | 2/2009 | Frigstad | A61F 2/0036 |
| | | | | 623/23.76 |
| 2011/0108039 | A1* | 5/2011 | Frigstad | A61F 6/22 |
| | | | | 128/831 |
| 2011/0130776 | A1* | 6/2011 | Jimenez | A61F 6/22 |
| | | | | 606/157 |
| 2013/0338625 | A1* | 12/2013 | Cully | A61M 5/00 |
| | | | | 604/500 |
| 2016/0106466 | A1 | 4/2016 | Gruber et al. | |
| 2017/0020729 | A1* | 1/2017 | Jarrett | A61L 31/16 |

* cited by examiner

FALLOPIAN BIOCOMPATIBLE PLUG WITH DIFFERENTLY EXPANDABLE PORTIONS

BACKGROUND

Field of the Invention

The exemplary and non-limiting embodiments described herein relate generally to devices and methods that relate to hysteroscopic procedures for the removal of uterine fibroids and other abnormal gynecological tissues. The exemplary and non-limiting embodiments described herein relate more particularly to surgical procedures pertaining to hysteroscopic tissue removal systems having fluid management and/or monitoring capabilities.

Brief Description of Prior Developments

It is believed that uterine fibroids occur in a substantial percentage of the female population, perhaps in at least 20 to 40 percent of all women. Uterine fibroids are well-defined, non-cancerous tumors that are commonly found in the smooth muscle layer of the uterus. In many instances, uterine fibroids can grow to be several centimeters in diameter and may cause symptoms like menorrhagia (prolonged or heavy menstrual bleeding), pelvic pressure or pain, and reproductive dysfunction. Hysteroscopy may be performed in either a physician's office with or without local anesthesia or in the operating room under monitored anesthesia care (MAC) or regional or general anesthesia. Hysteroscopy has been shown to be a safe and effective method for the treatment of, for example, uterine polyps, uterine adhesions, intrauterine septa, and abnormal uterine bleeding.

SUMMARY

In accordance with one aspect of the invention, a medical device assembly comprises: an endoscope having a working channel; a delivery tube configured to be received in the working channel; and a substantially cylindrical plug configured to be deliverable through a uterine cavity and into a fallopian tube of a patient by way of the delivery tube. The plug is configured to expand to internally seal the fallopian tube of the patient following its delivery into the fallopian tube.

In accordance with another aspect of the invention, a method comprises: delivering an endoscope into a uterine cavity of a patient; expanding or inflating the uterine cavity; and delivering a biocompatible plug from the endoscope into a fallopian tube of the patient. The biocompatible plug is configured to expand against an inner wall of the fallopian tube to seal the fallopian tube from the uterine cavity.

In accordance with another aspect of the invention, a method of treating a uterine abnormality of a patient comprises: providing an endoscope having a working channel; inflating a uterine cavity with a fluid; delivering a biocompatible plug into an ostium of a fallopian tube of the patient, wherein the biocompatible plug is substantially cylindrical in form and configured to be radially expandable, wherein the biocompatible plug is configured to expand in the ostium of the fallopian tube to seal the fallopian tube from the uterine cavity; delivering a resection device through the working channel; and resecting the uterine abnormality.

BRIEF DESCRIPTION OF THE DRAWINGS

The foregoing aspects and other features of the invention are explained in the following description, taken in connection with the accompanying drawings, wherein.

DETAILED DESCRIPTION

Hysteroscopy may be invaluable for diagnosing and treating the intrauterine cavity. Hysteroscopic procedures may be performed using an endoscope, with or without an attached integrated video imaging system, with the use of media suitable for distending the uterus. Examples of fluid media used to distend the uterus include, but are not limited to, liquids such as water or certain aqueous solutions (for example, a saline solution or Ringer's lactate solution) and gases. One exemplary method of distending the uterus using an appropriate gaseous medium involves insufflation or inflation or otherwise expanding with carbon dioxide ($CO_2$). Upon the distension of the uterus, the surgical procedure carried out may relate to hysteroscopic tissue removal such as the removal of uterine fibroids or other abnormal gynecological tissues.

Figure 1:
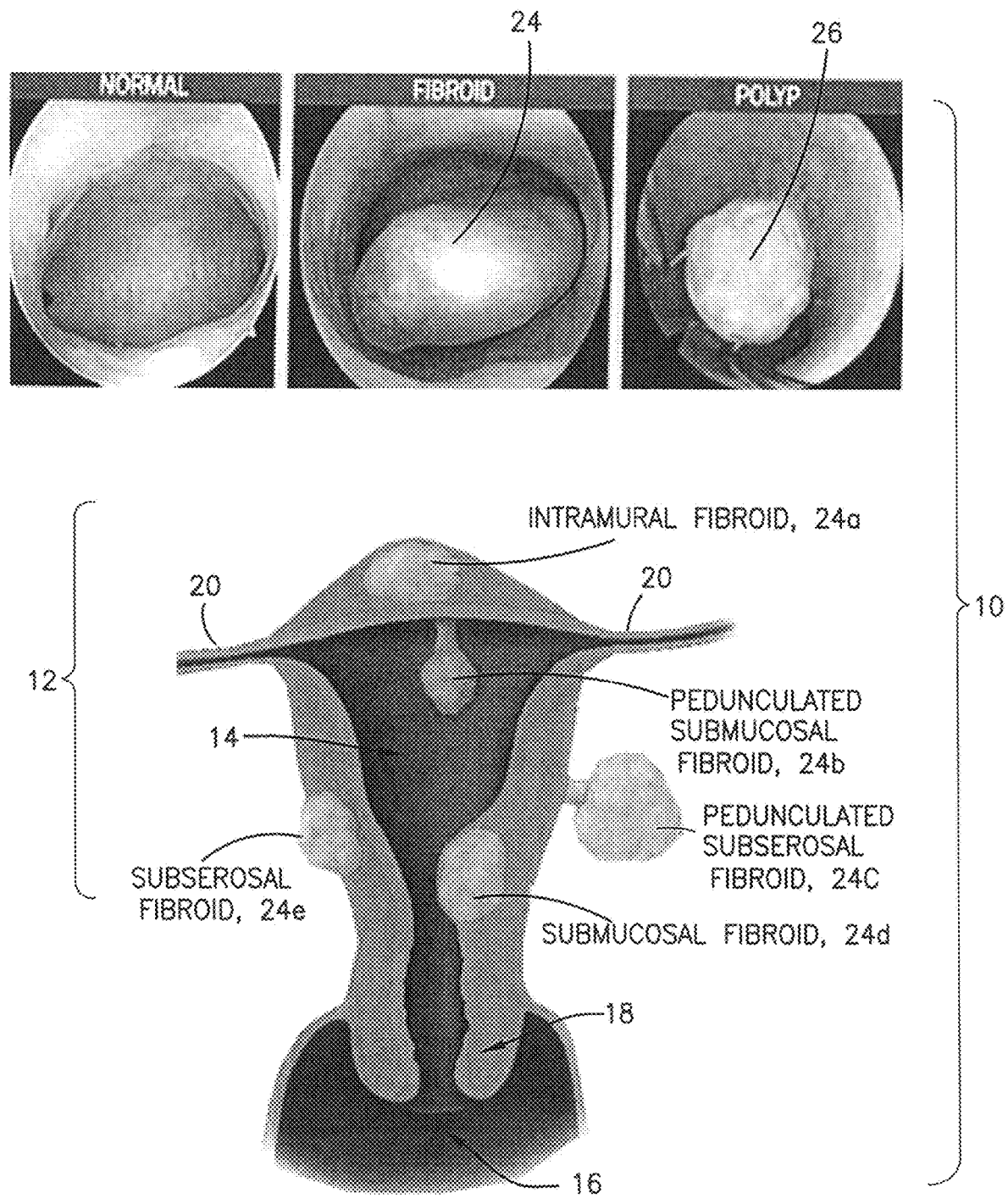
FIG. 1 is a schematic representation of a gynecological cavity having various tissue abnormalities.

Referring to FIG. 1, a gynecological cavity is shown and designated generally by the reference number 10. The gynecological cavity 10 includes the uterus 12 defining the uterine cavity 14, access to which is generally through the vaginal canal 16 and the cervix 18. The fallopian tubes 20 extend from an upper portion of the uterus 12 and terminate in fimbriated and funnel-shaped openings that wrap partway around the ovaries 22 (shown in FIG. 2).

It may be desirable in various situations for medical personnel to perform diagnostic and/or therapeutic procedures within the gynecological cavity 10. For example, as shown in FIG. 1, a surgeon may wish to detect, visualize, and/or treat conditions including, but not limited to, various tissue abnormalities such as fibroids 24, polyps 26, tumors, adhesions, or other tissue abnormalities within the uterus 12. Types of fibroids 24 include, but are not limited to, intramural fibroids 24a, pedunculated submucosal fibroids 24b, pedunculated subserosal fibroids 24c, submucosal fibroids 24d, subserosal fibroids 24e, and the like. The surgeon may also wish to treat endometriosis or other abnormal bleeding or fertility issues. To facilitate the visualization, detection, and/or, treatment of the above and like conditions, ample space may be needed within the gynecological cavity 10 for the procedure to be performed. Unfortunately, however, in those instances in which the gynecological cavity 10 is the uterine cavity 14, adequate space does not typically exist naturally. This is because the uterus 12 is a flaccid organ. As such, the walls of the uterus 12 are typically in contact with one another when in a relaxed state (similar to the walls of a deflated balloon). Consequently, active steps are generally taken to create a working space within the uterine cavity 14. One technique for creating such a working space is to administer a fluid medium to the uterine cavity 14, transcervically, under sufficient pressure to cause the uterus 12 to become distended.

Fluid media administered to the uterus 12 can be of low or high viscosity and of low or high molecular weight. The fluid media can also be either electrically conductive or nonconductive based upon the presence or absence of electrolytes in the fluid media. In terms of gaseous fluid media, it is generally accepted that $CO_2$ can be used as a distending medium for diagnostic hysteroscopy only as it may not be suitable for operative hysteroscopy or diagnostic procedures due to possible bleeding and the collection of blood and tissue debris, which may obscure the optical field of a viewing apparatus.

Figure 2:
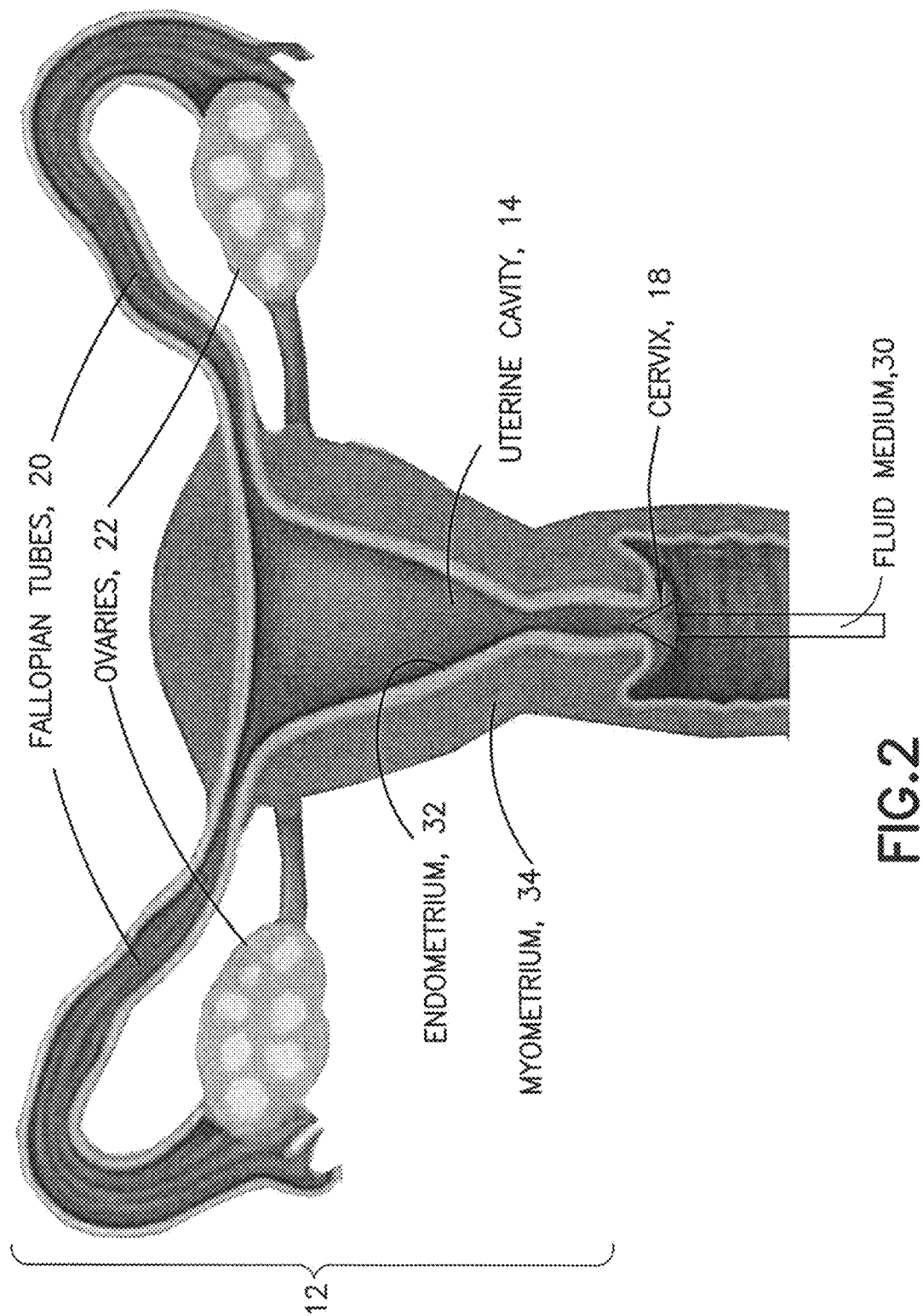
FIG. 2 is a schematic representation of a uterus having a fluid medium introduced thereto.

Referring now to FIG. 2, the fluid medium, shown generally at 30, may be introduced into the uterus 12 to cause the distension. While useful for the performance of hysteroscopy and hysteroscopically directed procedures, the distending fluid medium 30, if absorbed systemically in sufficient amounts, may have adverse effects on a patient. Consequently, understanding the physical properties and the potential risks associated with the use of the various fluid media used for distending the uterus 12 is beneficial for the safe performance of hysteroscopic procedures. For example, because the fluid medium 30 is administered under pressure (which pressure may be as great as 80-100 millimeters (mm) Hg or greater), there may be a risk of intravasation. Intravasation during hysteroscopy procedures is the absorption of the uterine distension media through the uterine vasculature, thus resulting in such fluids leaking through open uterine channels such as the ostium of the uterine tube or the fallopian tubes 20 where the fluid is then spilled to the peritoneal or abdominal cavity. Factors influencing the amount of intravasation can include, but are not limited to, intrauterine pressure; number and size of the vascular openings in the uterus; duration of the procedure; and the condition of the patient. In other cases, the principal mechanism of systemic absorption of the distending fluid medium 30 may be directly related to surgical disruption of the integrity of the venous sinuses in the deep endometrium 32 and the myometrium 34. Whether due to intravasation or surgical disruption, when these vessels or sinuses are transected, the fluid medium 30 is provided an opportunity to access the systemic circulation if the uterine pressure is greater than the patient's mean arterial pressure (MAP). Fluid overload in the patient can cause pulmonary edema or other undesirable effects. In terms of large amounts of $CO_2$ absorption, $CO_2$ is highly soluble in blood and if sufficiently high amounts reach the systemic circulation of the heart, $CO_2$ embolism may present, which may result in cardiorespiratory collapse.

To minimize the opportunities for the fluid medium to access the systemic circulation, intrauterine pressure should be controlled (for example, by close monitoring of the fluids administered) to maintain a balance between too much pressure, which increases the opportunity for fluid to leak into the patient's anatomy, and too little pressure, which decreases the visibility of the uterine cavity. The intrauterine pressure should remain below the patient's MAP. The MAP is the average pressure within an artery over a complete cycle of one heartbeat. Monitoring equipment in a hospital setting usually provides an automatic calculation of the MAP for the anesthesia personnel who can then report the reading to the operative team. In a physician's office, it may be necessary for medical personnel to manually calculate the patient's MAP using data from an automatic blood pressure monitor.

Figure 3:
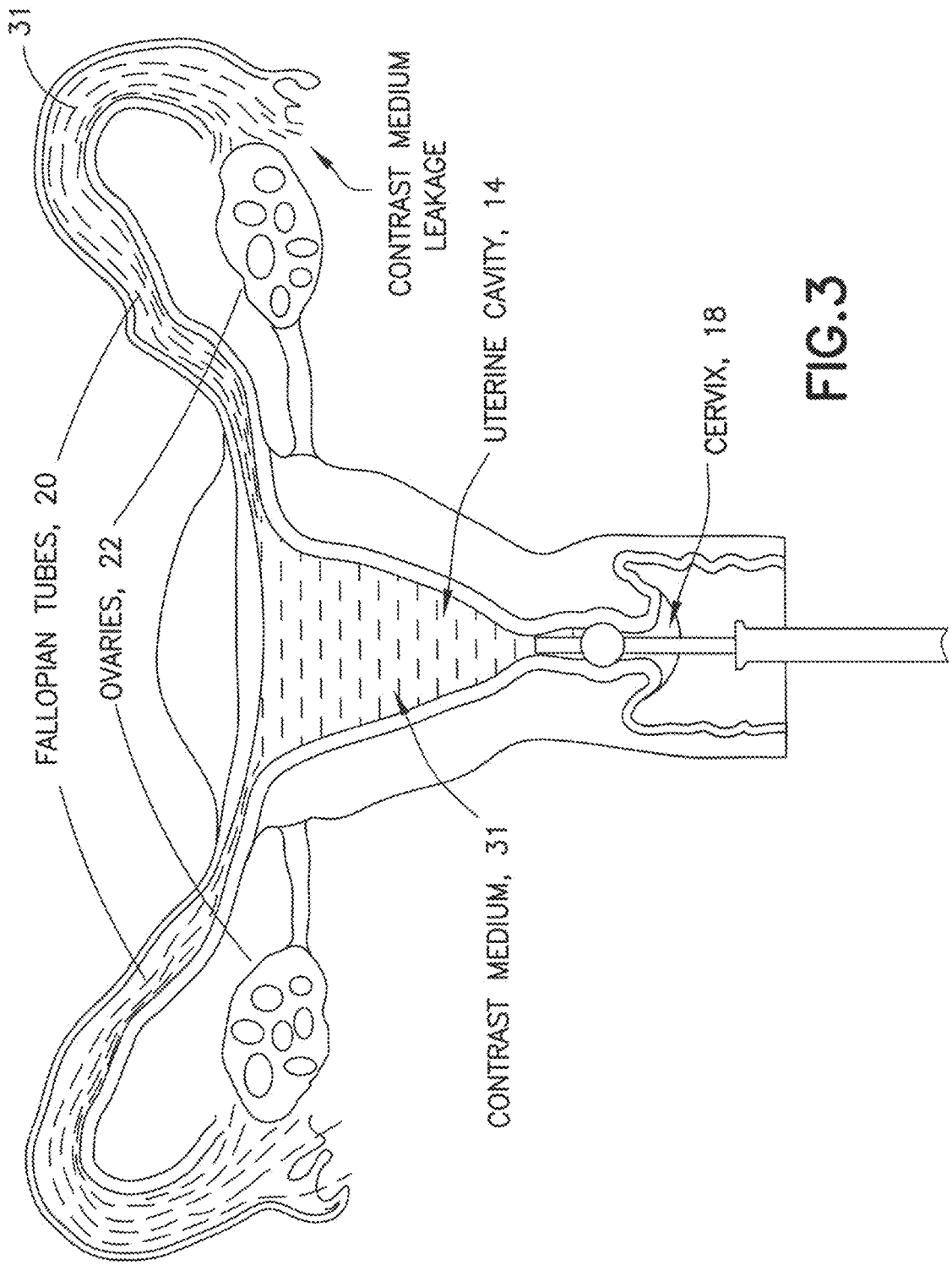
FIG. 3 is a schematic representation of a uterus having a contrast medium introduced thereto and contrast medium leakage from a fallopian tube.

Referring to FIG. 3, a determination of one mechanism by which pressurized fluid in the uterine cavity 14 may flow to the abdominal cavity through the fallopian tubes 20 may be carried out via contrast sonography. Contrast sonography may be performed on a patient during an office or outpatient visit and without an anesthetic. To carry out the procedure, a contrast medium 31 such as a sugar solution is injected into the uterine cavity 14 using a catheter. Movement of the contrast medium 31 is monitored using ultrasound, with the contrast medium 31 being monitored as it advances through the fallopian tube 20. Occasionally, it can only be presumed that the fallopian tubes 20 are open, such being the case when the contrast medium 31 flows out into the abdominal cavity even though the fallopian tubes 20 are not visible. The contrast sonography procedure is generally well-tolerated by most patients, with one side effect being discomfort in the abdominal region.

The AAGL (American Association of Gynecologic Laparoscopists) Practice Report Practice Guidelines for Management of Hysteroscopic Distending Media states:

"a. For healthy patients, the maximum fluid deficit of 1000 mL is suggested when using hypotonic solutions. This is based on a decrease in serum sodium of 10 mmol, with absorbed volume of around 1000 mL. The maximum limit for isotonic solution is unclear, but 2500 mL has been advocated in the previous AAGL Guidelines. Individualization and an opinion from an anesthesiologist should be obtained.

b. When high-viscosity distending media are used, the maximum infused volume should not exceed 500 mL, and in the elderly and those with cardiopulmonary compromise should not exceed 300 mL."

There are cases where hysteroscopic procedures are aborted due to a large fibroid 24 that needs to be removed but the fluid deficit was reached. The fluid deficit is characterized by the difference between the volume of distension fluid instilled into the uterine cavity 14 and the volume of fluid removed through the out-flow channel of a hysteroscope, plus fluid collected from the drapes or inadvertently lost in drapes and surrounding area of the operative table. The deficit closely represents the amount of fluid that may have been absorbed into the patient's vasculature.

Figure 4:
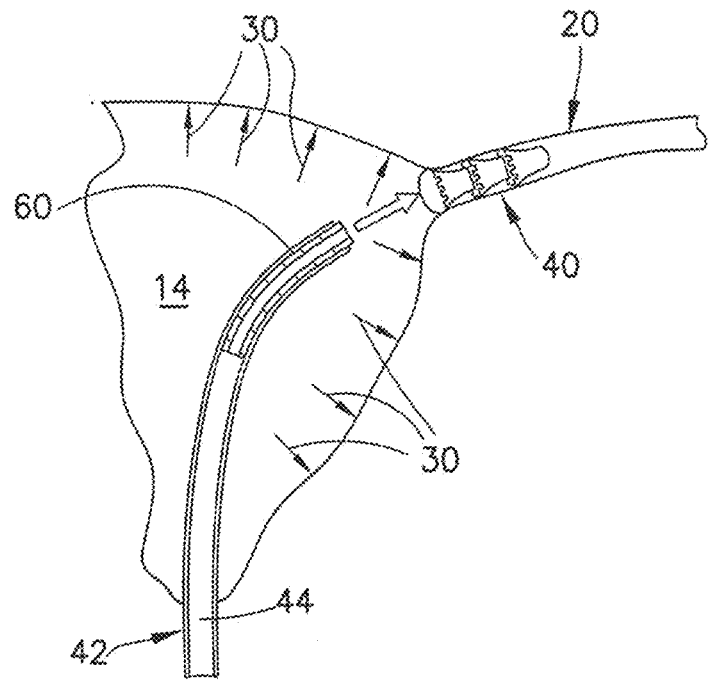
FIG. 4 is a schematic representation of one exemplary embodiment of a plug inserted into a fallopian tube.

Referring now to FIG. 4, one embodiment of a fallopian tube biocompatible plug (which may also be bioresorbable) is designated generally by the reference number 40 and is hereinafter referred to as "plug 40." The plug 40 is generally inserted using an endoscope such as a hysteroscope 42 (which may be flexible) in a hysteroscopic procedure, the plug 40 being introduced into the uterine cavity 14 transcervically through a delivery device such as a delivery tube 60 inserted through a working channel 44 of the hysteroscope 42, inserted into the fallopian tube 20, and expanded via the distension fluid (fluid medium 30) instilled into the uterine cavity 14. The plug 40 seals the fallopian tube 20 to prevent spillage of the fluid medium 30, which may be a saline solution, to the abdominal cavity. The plug may be fabricated of a material capable of being broken down by the body and not requiring mechanical removal from the uterine cavity 14 (similar to sutures and chlorhexidine chips). In the alternative, the material of the plug 40 may be mechanically removable from the uterine cavity 14, either by piecewise extraction or by being dissolved (for example, based on pH, enzymes, or temperature).

Materials from which the plug 40 may be fabricated include, but are not limited to, chitosan, cellulose, collagen, elastin, gelatin, keratin, various polymers such as polyethylene glycol (PEG), acrylates, alginates, and polymers of acrylic acids (such as CARBOPOL, available from Lubrizol Corporation of Wickliffe, Ohio, USA) combinations of the foregoing, and the like. Procedures used for the manufacture of the plug 40 include, but are not limited to, lyophilization, injection molding, UV crosslinking, chemical crosslinking (acid/base), and the like.

In one embodiment in which the material is expandable and dissolvable, the material may comprise N,O-carboxymethyl chitosan (about 85% to about 70%), methyl cellulose (about 10% to about 5%), hydroxyethyl cellulose (about 15% to about 5%), and xanthan gum (about 10% to about 1%), with an overall chemical dry weight being about 1.6% to about 3.0%. In one alternative, the material may comprise N,O-carboxymethyl chitosan (about 85% to about 65%), carboxymethyl cellulose (about 20% to about 5%), hydroxyethyl cellulose (15% to about 5%), and PEG (about 20% to about 1%), again with an overall chemical dry weight being about 1.6% to about 3.0%. In another alternative, the material may comprise N,O-carboxymethyl chitosan (about 85% to about 65%), sodium polyacrylate (about 20% to about 5%), calcium alginate (about 20% to about 1%), and hydroxyethyl cellulose (about 15% to about 5%), again with an overall chemical dry weight being about 1.6% to about 3.0%.

In another embodiment in which the material is non-expandable and dissolvable, the material may comprise N,O-carboxymethyl chitosan, polyacrylic acid, and methyl cellulose.

In another embodiment in which the material is non-expandable and non-dissolvable, the material may comprise silicone and a modified chitosan plug.

Figure 5:
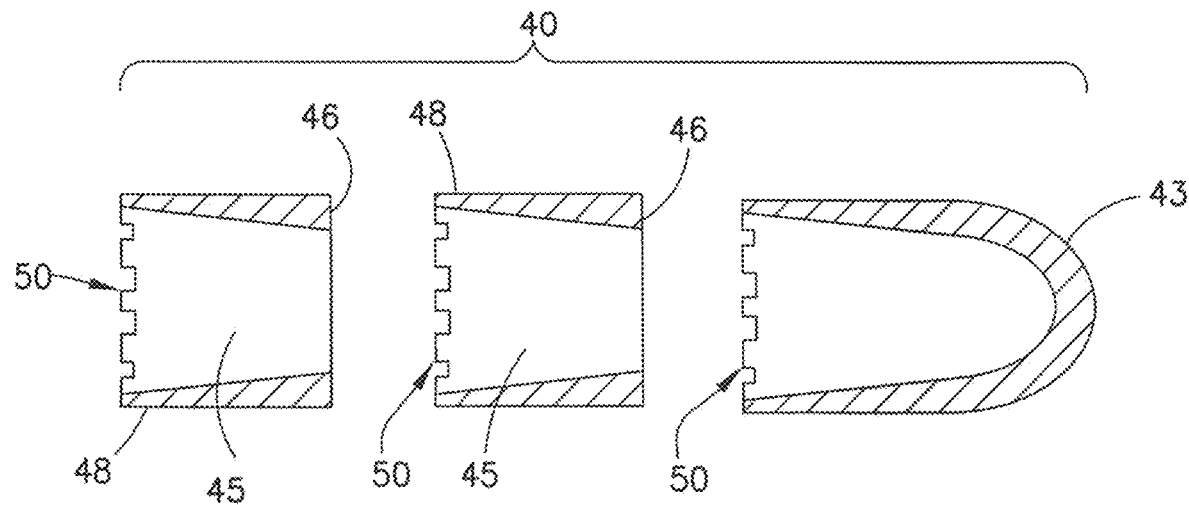
FIG. 5 is an exploded view of the plug of FIG. 4.
Figure 6:
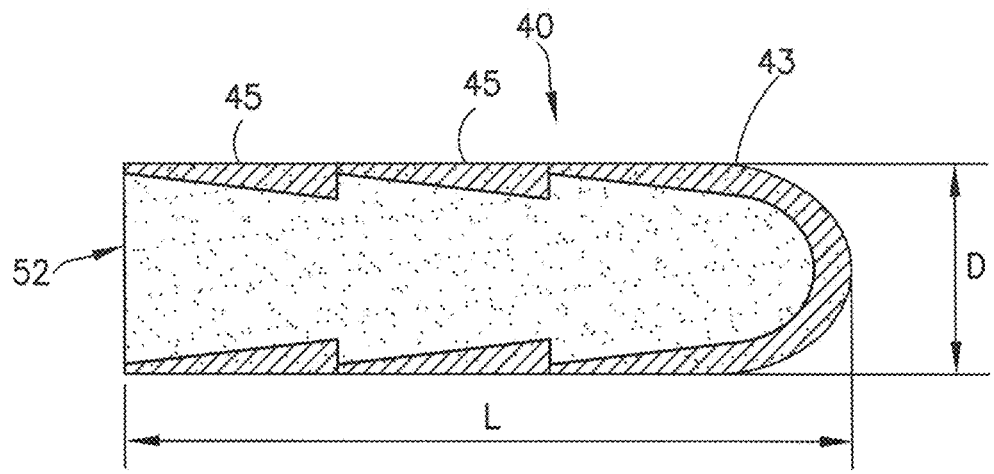
FIG. 6 is a side sectional view of the plug of FIG. 4.
Figure 7:
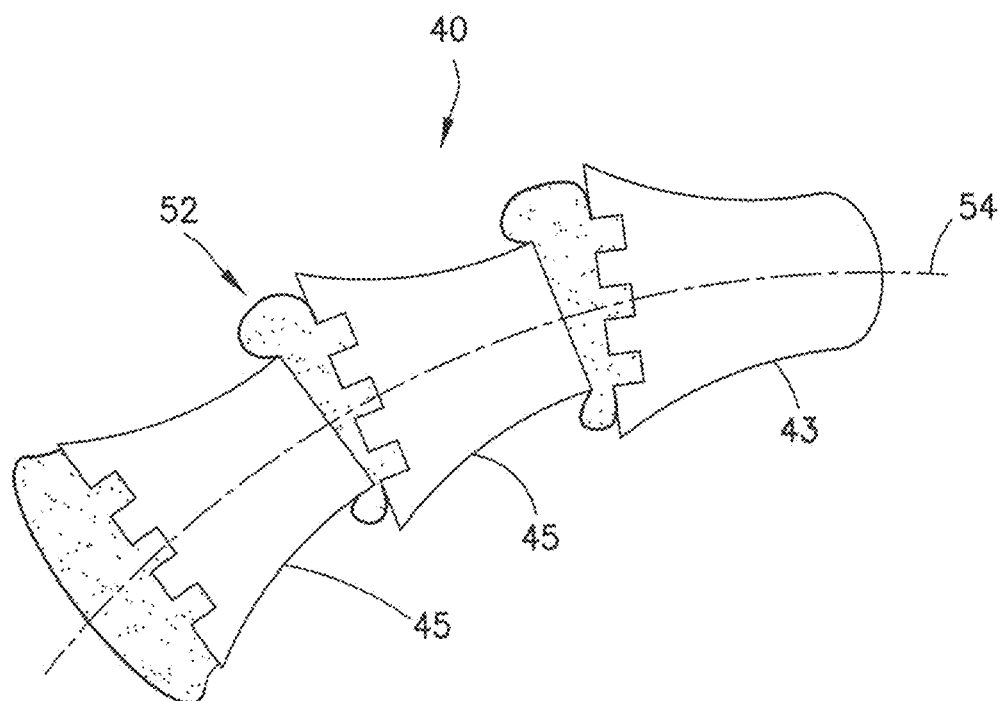
FIG. 7 is a side view of the plug of FIG. 4 showing radial expansion and longitudinal curvature.

Referring now to FIGS. 5 through 7, the plug 40 comprises a nose portion 43 and one or more body portions arranged end-to-end to form an elongated member suitable for insertion into the ostium of the fallopian tube 20. Although two body portions 45 are illustrated, any suitable number of body portions 45 may be employed. The nose portion 43 may be a substantially cylindrical member closed at the forward end and suitably rounded. Each of the body portions 45 may be ring-shaped. Walls of both the nose portion 43 and the body portions 45 may be tapered with leading edges 46 being thicker than trailing edges 48. The materials of the nose portion 43 and the body portions 45 may be formed as closed cell foams.

As shown in FIG. 5, the trailing edges 48 of the body portions 45 as well as the nose portion 43 may include end slots 50. In embodiments in which the fluid medium 30 is a saline solution, the end slots 50 allow fluid ingress.

As shown in FIG. 6, the nose portion 43 and the body portions 45 may be arranged over a flexible mandrel 52 and frictionally retained thereon. The leading edges 46 of the body portions 45 are generally engaged with the trailing edges 48 of the more forward piece, such as another body portion 45 or the nose portion 43. Once assembled, the diameter D of the plug 40 may be about 0.15 inches (in.) to about 0.2 in., and a length L of the plug 40 may be about 0.75 in. to about 1.0 in.

As shown in FIG. 7, the flexibility of the mandrel 52 may allow the nose portion 43 and body portions 45 to bend out of alignment along a longitudinal curvature 54, thereby conforming to a curvature of the ostium of the fallopian tube 20. The materials of the mandrel 52 may be formed as expandable open cell foams.

Figure 8:
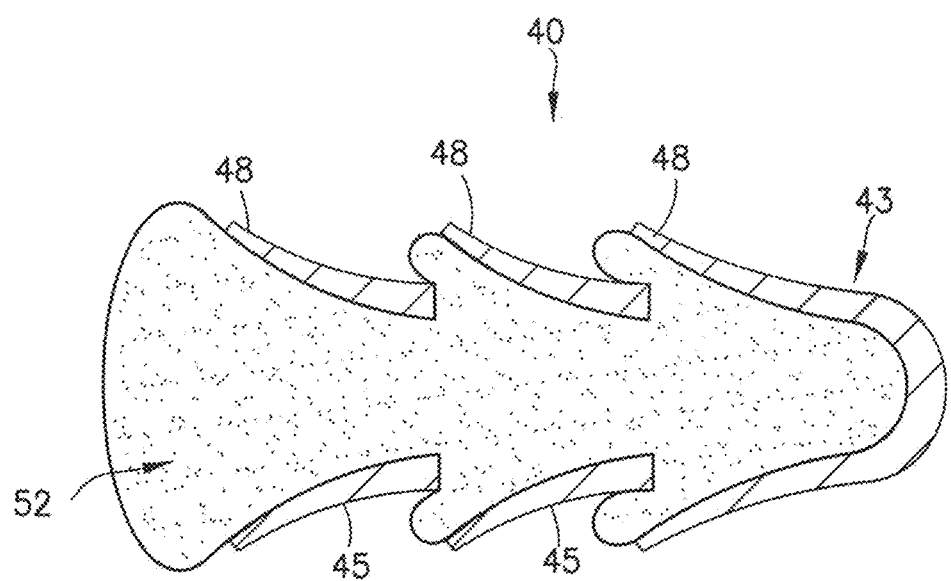
FIG. 8 is a side sectional view of the plug of FIG. 4 showing expansion of select portions of the plug.
Figure 9:
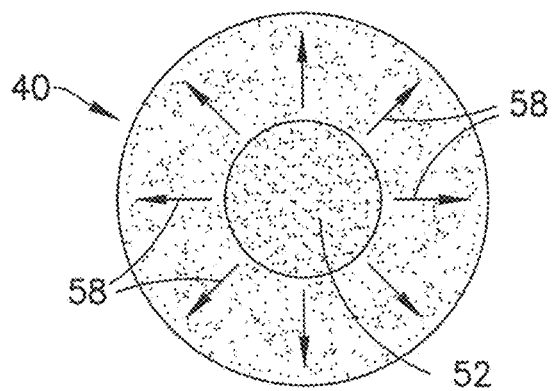
FIG. 9 is a cross sectional view of a mandrel of the plug showing radial expansion.

Referring now to FIGS. 8 and 9, the material of the mandrel 52 may be expandable in radial directions about 1.5 to about 2 times from the original diameter upon an application of moisture (for example, from the saline solution or other fluid medium 30) and/or heat. As shown in FIG. 8, the reduced thicknesses of the walls proximate the trailing edges 48 of the nose portion 43 and the body portions 45 may facilitate increased radial expansion of the plug 40 with material of the mandrel 52 being exuded from openings formed by the radial expansion of the trailing edges 48, thus resulting in barbed features being formed along the length of the plug 40. The barbed features allow the plug 40 to be anchored in place in the ostium of the fallopian tube 20 and sealed against the walls of the ostium. As can be seen in FIG. 9, the material of the mandrel 52 may expand in radial directions 58 to push the trailing edges 48 outward to anchor the plug 40 and seal the fallopian tube 20.

Figure 10:
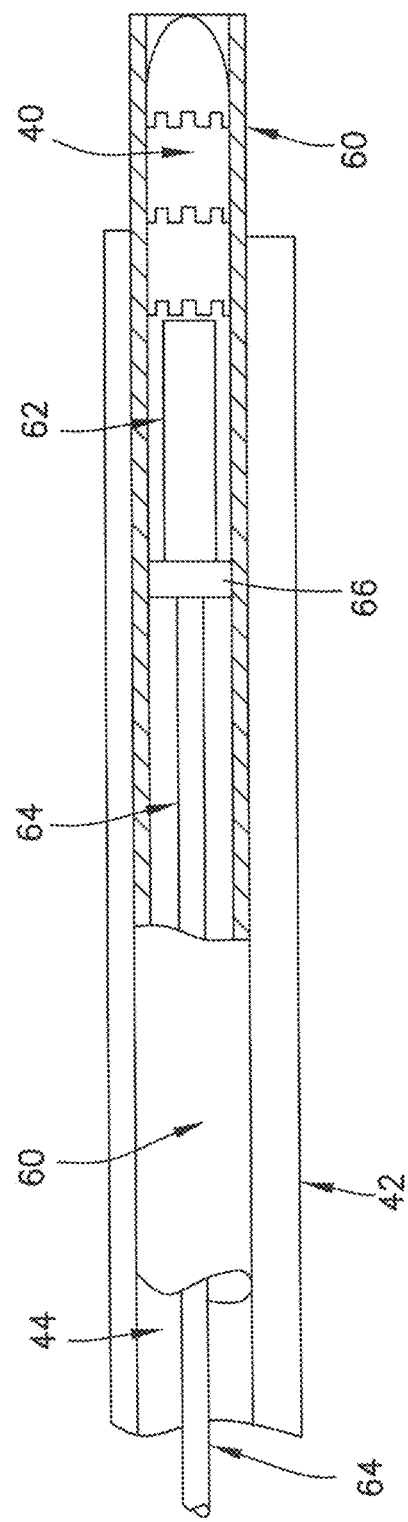
FIG. 10 is a side sectional view of a hysteroscope showing a delivery tube in a working channel and the plug in the delivery tube.

Referring now to FIG. 10, to apply the plug 40 to the fallopian tube 20, the plug 40 may be inserted from the delivery tube 60 at a distal end of the working channel 44 of the hysteroscope 42. The plug 40 may be dispensed from the delivery tube 60 using a piston 62 made operable by a push cable 64. The piston 62 may include a base 66, with the push cable 64 being coupled to a rearward end of the base 66. The base 66 has an outer circumference that is frictionally engaged with inner walls of the delivery tube 60, but which may be configured td maintain a gas-tight seal. The plug 40 may be frictionally retained in the distal end of the delivery tube 60 forward of the piston 62. At this point, the mandrel 52 is sealed by the outer walls of the nose portion 43 and the body portions 45 of the plug 40 such that the material of the mandrel 52 is not exposed to the fluid medium 30.

Figure 11:
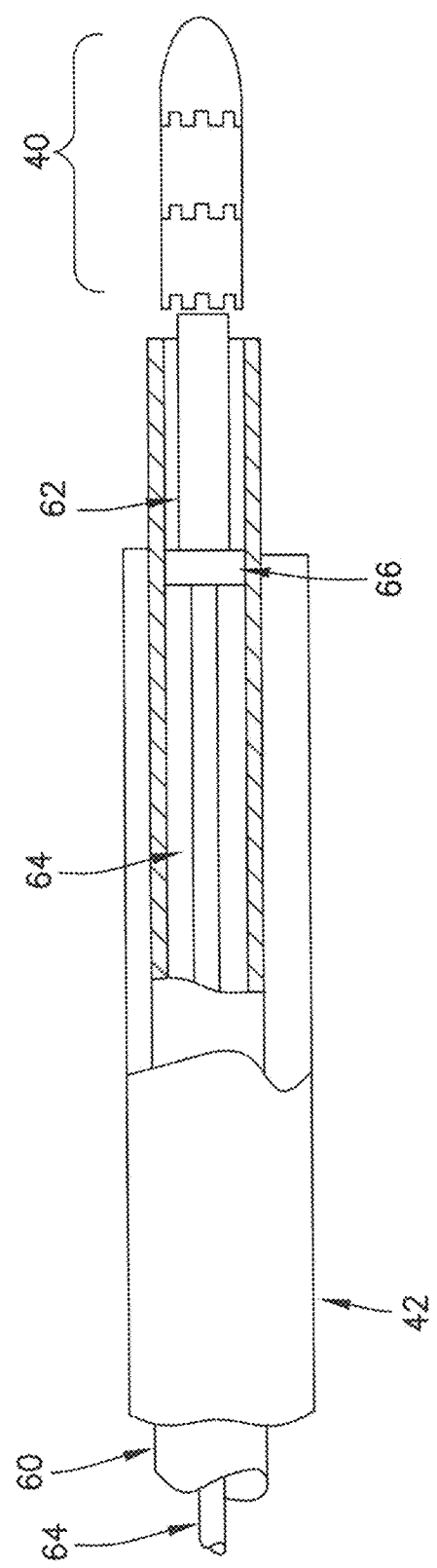
FIG. 11 is a side sectional view of the hysteroscope of FIG. 10 showing the plug being deployed from the delivery tube.

Referring now to FIG. 11, application of the plug 40 may involve translating the delivery tube 60, the piston 62, and the plug 40 as an assembly through the working channel 44 to a distal end of the hysteroscope 42 when the distal end of the hysteroscope 42 is positioned at the fallopian tube 20. Once the assembly of the delivery tube 60, the piston 62, and the plug 40 is at the distal end of the hysteroscope 42 and the plug 40 is ready to be deployed, the push cable 64, which may be a stiff wire, is pushed forward to move the piston 62 forward until the piston 62 reaches the end of the delivery tube 60, thus pushing the plug 40 out of the delivery tube 60 and into the fallopian tube 20. As the plug 40 is exposed to the fluid medium 30, the material of the mandrel 52 absorbs the fluid medium 30 and expands accordingly. It should be understood, however, that the plug 40 is not limited to being introduced into the fallopian tube 20 through the uterine cavity 14, as the plug 40 may be introduced laparoscopically into the ostium of the fallopian tube 20.

Figure 12:
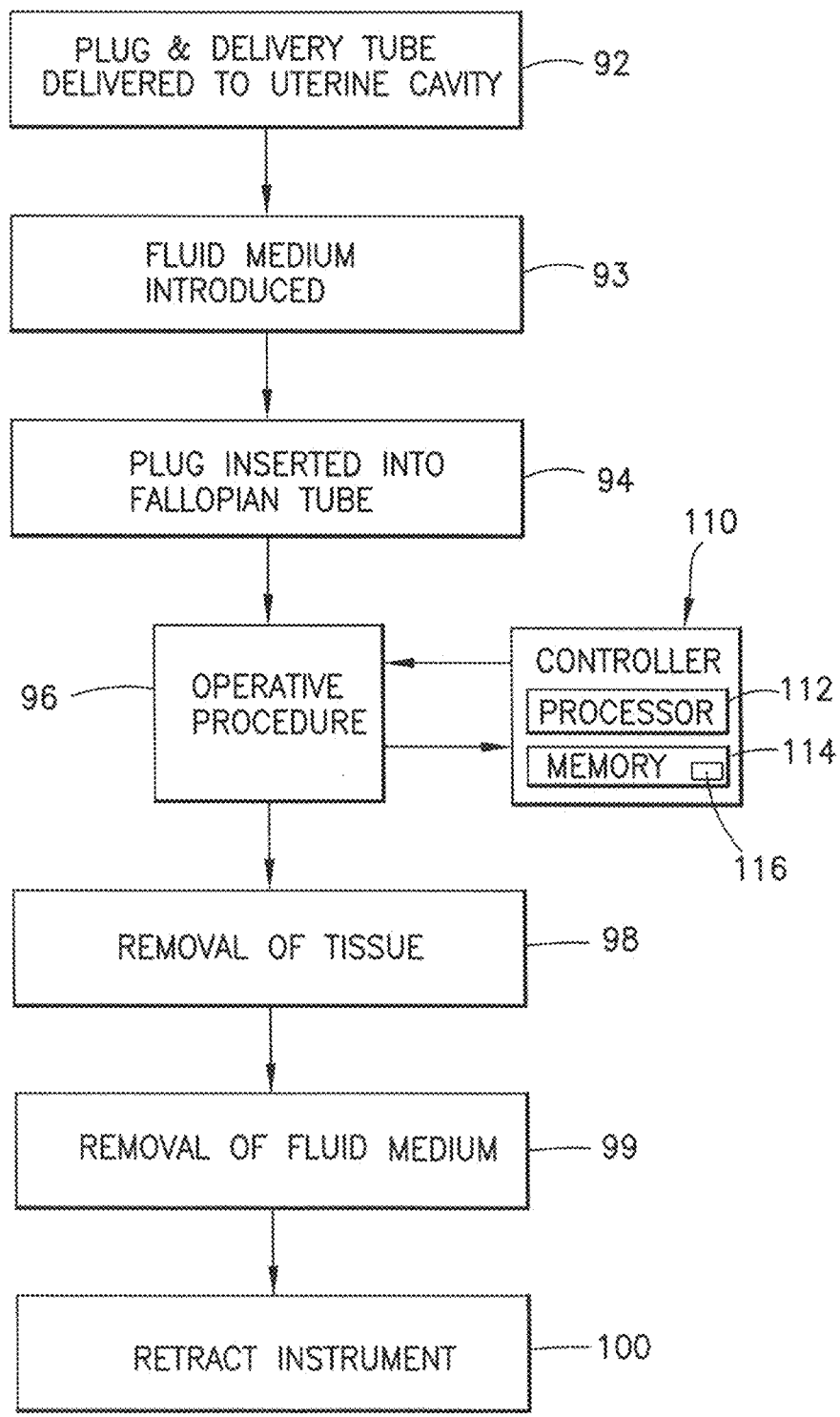
FIG. 12 is a flow of one exemplary embodiment of a method of performing a hysteroscopic procedure using a biocompatible fallopian tube plug.

Referring to FIG. 12, a flow of one exemplary method of using the plug 40 in conjunction with a hysterocope 42 is shown generally at 90 and is hereinafter referred to as "method 90." In the method 90, the plug 40 and the delivery tube 60 are installed onto the hysteroscope 42 and delivered into the uterine cavity 14, in a step 92. In a step 93, the fluid medium 30 may be introduced through the working channel 44 of the hysteroscope 42 to inflate or expand the uterus.

After inflation or expansion of the uterine cavity 14, the plug 40 is inserted into the fallopian tube 20 and expanded. Instruments that also may be introduced include, but are not limited to, viewing instruments such as cameras and lighting equipment (if not already present on the hysteroscope 42) having working channels for the introduction of further instruments such as tissue removal device blades, fluid flow devices, and the like. After inserting the instruments, an operative procedure may be carried out in an operation step 96. The operation step 96 may comprise the resecting of tissue using the tissue removal device blade. In a removal step 98, any tissue (such as resected tissue pertaining to an abnormality) may be removed through a suction path of the tissue removal device blade. In a fluid removal step 99, the fluid medium 30 may be removed. Following removal of tissue (if tissue was resected) and/or the fluid medium 30, the instruments may be retracted in a retraction step 100.

Any of the foregoing step may be carried out using a robot or robotic apparatus and controlled using a controller 110 having a processor 112 and a memory 114, the memory 114 having software 116. Although the operation step 96 is shown as being controlled using the controller 110, it should be understood that any of the described steps could be carried out robotically and using the controller 110.

Referring to all the Figures, the proposed invention provides a seal in the uterine cavity by implementing a plug that blocks the pathway into the fallopian tubes to prevent saline (or other fluid) spillage to the abdominal cavity.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

In one exemplary embodiment, a medical device assembly comprises: an endoscope having a working channel; a delivery tube configured to be received in the working channel; and a substantially cylindrical plug configured to be deliverable through a uterine cavity and into a fallopian tube of a patient by way of the delivery tube. The plug is configured to expand to internally seal the fallopian tube of the patient following its delivery into the fallopian tube.

The plug may be biocompatible and/or bioresorbable. The plug may be fabricated from one or more of chitosan, cellulose, collagen, elastin, gelatin, keratin, and polymer. The plug may comprise a nose portion, at least one body portion, and a substantially cylindrical mandrel, the nose portion comprising a substantially cylindrical member closed at a forward end, and the at least one body portion comprising a ring member having a forward end arranged against a rearward end of the nose portion, wherein the nose portion and the at least one body portion are mounted on an outside of the mandrel. The mandrel may be configured to expand relative to the nose portion and the at least one body portion to expand the rearward end of the nose portion and a rearward end of the at least one body portion. The nose portion and the at least one body portion may be formed as a closed cell foam, and the mandrel may be formed as an open cell foam. Material at the rearward end of the nose portion may be thinner relative to material at the forward end of the nose portion, and material at a rearward end of the at least one body portion may be thinner relative to material at the forward end of the at least one body portion. An expansion of material of the mandrel may be configured to cause a radial expansion of the rearward end of the nose portion and a radial expansion of the rearward end of the at least one body portion.

In another exemplary embodiment, a method comprises: delivering an endoscope into a uterine cavity of a patient; inflating or expanding the uterine cavity; and delivering a biocompatible plug from the endoscope into a fallopian tube of the patient. The biocompatible plug is configured to expand against an inner wall of the fallopian, tube to seal the fallopian tube from the uterine cavity.

The method may further comprise using a piston to deliver the biocompatible plug into the fallopian tube. The method may further comprise using a wire to move the piston to deliver the biocompatible plug into the fallopian tube. Expanding the biocompatible plug against an inner wall of the fallopian tube may comprise expanding selected portions of the biocompatible plug. Expanding selected portions of the biocompatible plug may comprise expanding a mandrel around which the biocompatible plug is mounted. The method may further comprise allowing at least a portion of the biocompatible plug to resorb into the uterine cavity of the patient.

In another exemplary embodiment, a method of treating a uterine abnormality of a patient comprises: providing an endoscope having a working channel; inflating a uterine cavity with a fluid; delivering a biocompatible plug into an ostium of a fallopian tube of the patient, wherein the biocompatible plug is substantially cylindrical in form and configured to be radially expandable, wherein the biocompatible plug is configured to expand in the ostium of the fallopian tube to seal the fallopian tube from the uterine cavity; delivering a resection device through the working channel; and resecting the uterine abnormality.

Delivering a biocompatible plug may comprise delivering the biocompatible plug from a delivery device in the working channel using a piston to push the biocompatible plug out of the delivery device. Delivering a biocompatible plug may comprise delivering the biocompatible plug laparoscopically to the uterine cavity. Expanding the biocompatible plug in the ostium of the fallopian tube may comprise radially expanding select portions of the biocompatible plug. Radially expanding select portions of the biocompatible plug may comprise expanding a foam mandrel on which the biocompatible plug is mounted. The method may further comprise allowing the biocompatible plug to resorb into the uterine cavity of the patient. The method may further comprise removing the fluid from the uterine cavity.

It should be understood that the foregoing description is only illustrative of the invention. Various alternatives and modifications can be devised by those skilled in the art without departing from the invention. Accordingly, the invention is intended to embrace all such alternatives, modifications, and variances which fall within the scope of the appended claims.

What is claimed is:

1. A medical device for use with assembly comprising an endoscope having a working channel and a delivery tube configured to be received in the working channel, the device, comprising:

a substantially cylindrical plug configured to be deliverable through a uterine cavity and into a fallopian tube of a patient by way of the delivery tube, the plug including a substantially cylindrical mandrel flexible in a longitudinal direction, a nose portion comprising a closed forward end and a substantially cylindrical member, and at least one body portion comprising a ring member having a forward end arranged against a rearward end of the nose portion, the nose portion and the at least one body portion mounted on an outer surface of the mandrel;

wherein the plug is configured to expand to internally seal the fallopian tube of the patient following its delivery into the fallopian tube;

wherein the flexibility of the mandrel allows the nose portion and the at least one body portion to bend out of alignment in the longitudinal direction, conforming to a curvature of the fallopian tube; and wherein at least one of:
- a first portion of the mandrel is configured to expand relative to the nose portion to expand the rearward end of the nose portion and a second portion of the mandrel is configured to expand relative to the at least one body portion to expand a rearward end of the at least one body portion; or
- material at the rearward end of the nose portion is configured to expand more relative to material at the forward end of the nose portion, and wherein material at a rearward end of the at least one body portion is configured to expand more relative to material at the forward end of the at least one body portion.

2. The medical device of claim 1, wherein the plug is biocompatible.

3. The medical device of claim 2, wherein the plug is bioresorbable.

4. The medical device of claim 1, wherein the plug is fabricated from one or more of chitosan, cellulose, collagen, elastin, gelatin, keratin, and polymer.

5. The medical device of claim 1, further comprising at least one of the endoscope or the delivery tube.

6. The medical device of claim 1, wherein material at the rearward end of the nose portion is configured to expand more relative to material at the forward end of the nose portion, and wherein material at a rearward end of the at least one body portion is configured to expand more relative to material at the forward end of the at least one body portion.

7. The medical device of claim 6, wherein an expansion of material of the mandrel is configured to cause a radial expansion of the rearward end of the nose portion and a radial expansion of the rearward end of the at least one body portion.

8. The medical device assembly of claim 5, wherein the forward end of the nose portion is rounded.

9. The medical device assembly of claim 5, wherein the nose portion is tapered such that the forward end is thicker than the rearward end.

10. The medical device assembly of claim 9, wherein the at least one body portion is tapered such that the forward end is thicker than a rearward end thereof.

11. The medical device of claim 1, wherein a first portion of the mandrel is configured to expand relative to the nose portion to expand the rearward end of the nose portion and a second portion of the mandrel is configured to expand relative to the at least one body portion to expand a rearward end of the at least one body portion.

12. The medical device assembly of claim 1, wherein the nose portion and the at least one body portion of the plug are fabricated from a closed cell foam.

13. The medical device assembly of claim 12, wherein the mandrel is fabricated from an open cell foam.

14. The medical device assembly of claim 1, wherein the rearward end of the nose portion and a rearward end of the at least one body portion each comprise a plurality of end slots.

15. The medical device assembly of claim 1, wherein the nose portion and the at least one body portion are frictionally retained on the outer surface of the mandrel.

16. The medical device assembly of claim 1, wherein the plug has a diameter between about 0.15 inches and about 0.2 inches, and wherein the plug has a length between about 0.75 inches and about 1.0 inches.

17. The medical device assembly of claim 1, wherein the mandrel is expandable to form a barb feature between the rearward end of the nose portion and the forward end of the at least one body portion.

18. A medical device assembly, comprising:
an endoscope having a working channel;
a delivery tube configured to be received in the working channel; and
a substantially cylindrical plug comprising a substantially cylindrical mandrel flexible in a longitudinal direction and configured to be deliverable through a uterine cavity and into a fallopian tube of a patient by way of the delivery tube;
wherein the plug is configured to expand to internally seal the fallopian tube of the patient following its delivery into the fallopian tube;
wherein the plug comprises a nose portion and at least one body portion on the substantially cylindrical mandrel, the nose portion comprising a substantially cylindrical member closed at a forward end, and the at least one body portion comprising a ring member having a forward end arranged against a rearward end of the nose portion, wherein the nose portion and the at least one body portion are mounted on an outside of the mandrel; and
wherein a first portion of the mandrel is configured to expand relative to the nose portion to expand the rearward end of the nose portion and a second portion of the mandrel is configured to expand relative to the at least one body portion to expand a rearward end of the at least one body portion.

19. A medical device assembly, comprising:
an endoscope having a working channel;
a delivery tube configured to be received in the working channel; and
a substantially cylindrical plug comprising a substantially cylindrical mandrel flexible in a longitudinal direction and configured to be deliverable through a uterine cavity and into a fallopian tube of a patient by way of the delivery tube;
wherein the plug is configured to expand to internally seal the fallopian tube of the patient following its delivery into the fallopian tube;
wherein the plug comprises a nose portion and at least one body portion on the substantially cylindrical mandrel, the nose portion comprising a substantially cylindrical member closed at a forward end, and the at least one body portion comprising a ring member having a forward end arranged against a rearward end of the nose portion, wherein the nose portion and the at least one body portion are mounted on an outside of the mandrel; and
wherein material at the rearward end of the nose portion is configured to expand more relative to material at the forward end of the nose portion, and wherein material at a rearward end of the at least one body portion is configured to expand more relative to material at the forward end of the at least one body portion.

20. The medical device assembly of claim 19, wherein an expansion of material of the mandrel is configured to cause a radial expansion of the rearward end of the nose portion and a radial expansion of the rearward end of the at least one body portion.

\* \* \* \* \*